United States Patent
Jacobs

(10) Patent No.: US 10,751,403 B2
(45) Date of Patent: Aug. 25, 2020

(54) **VACCINE FOR PROTECTION AGAINST *STREPTOCOCCUS SUIS***

(71) Applicant: Intervet Inc., Madison, NJ (US)

(72) Inventor: Antonius Arnoldus Christiaan Jacobs, Kessel (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/386,783

(22) Filed: Apr. 17, 2019

(65) Prior Publication Data

US 2019/0336594 A1 Nov. 7, 2019

(30) Foreign Application Priority Data

Apr. 3, 2018 (EP) ...................................... 18165381

(51) Int. Cl.
*A61K 39/09* (2006.01)
*A61K 39/00* (2006.01)
*A61K 49/00* (2006.01)

(52) U.S. Cl.
CPC ...... *A61K 39/092* (2013.01); *A61K 2039/552* (2013.01)

(58) Field of Classification Search
CPC .............................. A61K 39/00; A61K 39/092
USPC ......................................... 424/9.1, 9.2, 234.1
See application file for complete search history.

(56) References Cited

U.S. PATENT DOCUMENTS

2017/0209561 A1* 7/2017 Seele .................. A61K 39/092

FOREIGN PATENT DOCUMENTS

| EP | 2949340 A1 | 12/2015 |
| WO | 2010/108977 A1 | 9/2010 |
| WO | 2017/005913 A1 | 1/2017 |

OTHER PUBLICATIONS

Segura, M., Expert Review of Vaccine, 2015, vol. 14, Issue 12, pp. 1587-1608.*
Baums, C et al, Immunogenicity of an Autogenous *Streptococcus suis* Bacterin in Preparturient Sows and Their Piglets in Relation to Protection after Weaning†, Clinical and Vaccine Immunology, 2010, pp. 1589-1597, vol. 17, No. 10, WO.
European search report for application 18165381.7 dated Jul. 9, 2018.
Seele, J et al, The immunoglobulin M-degrading enzyme of *Streptococcus suis*, IdeSsuis, is a highly protective antigen against serotype 2, Vaccine, 2015, pp. 2207-2212, vol. 33 No. 19, Elsevier, EP.

* cited by examiner

*Primary Examiner* — Rodney P Swartz

(57) ABSTRACT

The present invention pertains to a vaccine comprising an IgM protease antigen of *Streptococcus suis*, for use in a method wherein a female pig is vaccinated in order to protect a piglet against *Streptococcus suis* through the intake of colostrum of the vaccinated female pig.

13 Claims, 1 Drawing Sheet

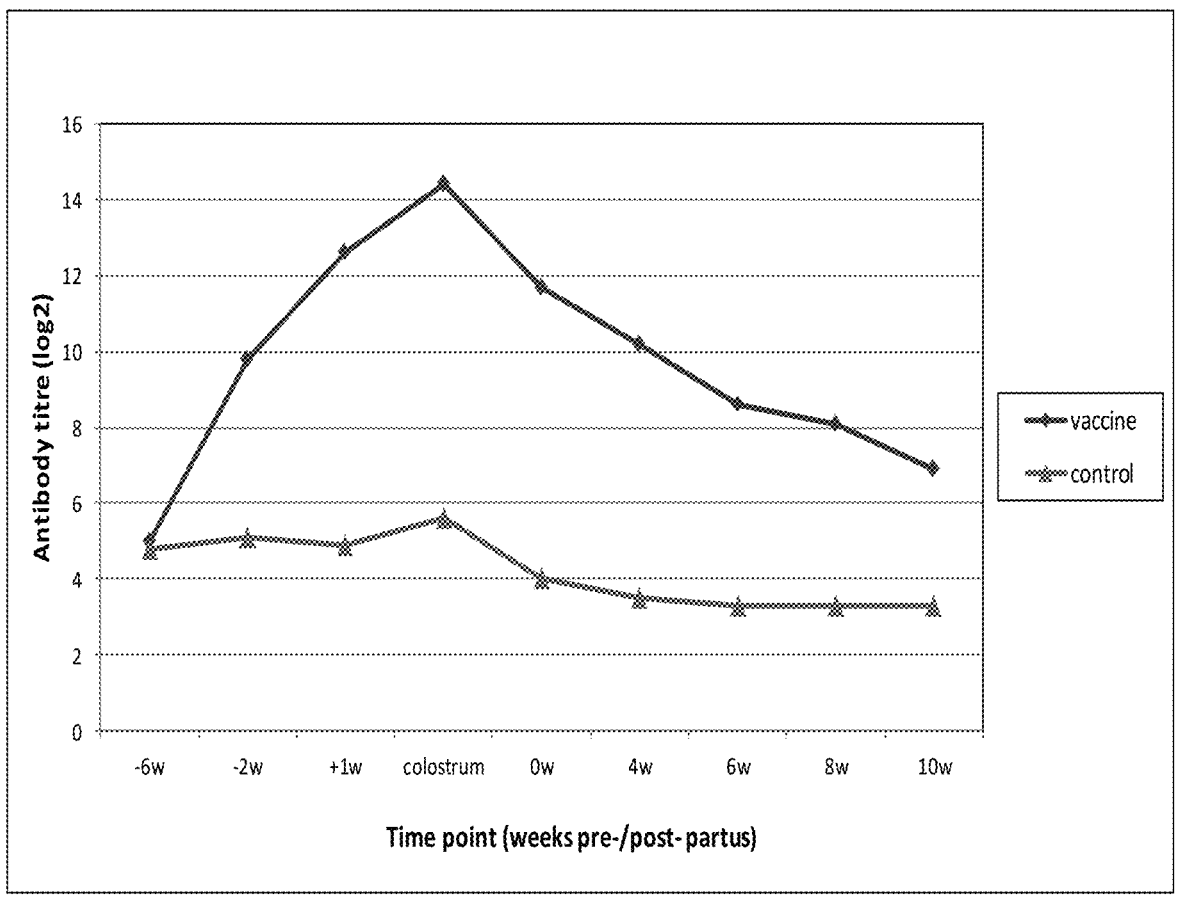

VACCINE FOR PROTECTION AGAINST STREPTOCOCCUS SUIS

CROSS-REFERENCE TO RELATED APPLICATIONS

This application claims the benefit of priority from EP Application No. EP18165381.7, filed on Apr. 3, 2018, which is hereby incorporated herein by reference in its entirety.

GENERAL FIELD OF THE INVENTION

The invention pertains to the protection of young piglets against a pathogenic infection with Streptococcus suis.

BACKGROUND OF THE INVENTION

Streptococcus suis (S suis) is a commensal and opportunistic pathogen of swine. In particular under stress, the bacterium may elicit a pathogenic infection and induce disease. Under modern pig producing conditions, major stress is induced for example by weaning of piglets and transport of young piglets. This has made Streptococcus suis to become a major swine pathogen. It is also an emerging zoonotic agent of human meningitis and streptococcal toxic shock-like syndrome. Streptococcus suis is a well-encapsulated pathogen and multiple serotypes have been described based on the capsular polysaccharide antigenic diversity. Streptococcus suis uses an arsenal of virulence factors to evade the host immune system. Together, these characteristics have challenged the development of efficacious vaccines to fight this important pathogen. Recently, an overview article has been published regarding vaccines against Streptococcus suis (Mariela Segura: "Streptococcus suis vaccines: candidate antigens and progress, in Expert Review of Vaccines, Volume 14, 2015, Issue 12, pages 1587-1608). In this review, clinical field information and experimental data have been compiled and compared to give an overview of the current status of vaccine development against Streptococcus suis as outlined here below.

Currently used vaccines are mainly whole-cell bacterins. However, field reports describe difficulty in disease control and management, and specially "vaccine failures" are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Early medicated weaning and segregated early weaning practices do not eliminate Streptococcus suis infection. Therefore, effective control measures to prevent disease will hinge on prophylactic/metaphylactic procedures (where allowed) and on vaccination. Currently, field immunization efforts have focused on the use of commercial or autogenous bacterins. These vaccine strategies have been applied to either piglets or (adult) female animals (gilts and sows). From weaning and onwards piglets are more susceptible to Streptococcus suis infections due to the stresses associated with weaning and also, the common subsequent transport. Therefore, prepartum immunization in female animals (commonly referred to as "sow vaccination") is often used to try and convey passive immunity to piglets and provide protection against Streptococcus suis under these stressful circumstances early in life. Moreover, sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide adequate protection in the most critical period of 4-7 weeks of age.

In piglets, autogenous bacterins are frequently used in the field, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent.

Other experimental vaccines are also described in the art. Kai-Jen Hsueh et al. show ("Immunization with Streptococcus suis bacterin plus recombinant Sao protein in sows conveys passive immunity to their piglets", in: BMC Veterinary Research, BMC series—open, inclusive and trusted, 13:15, 7 Jan. 2017) that a bacterin plus subunit might be a basis for successful vaccination of sows to confer protective immunity to their piglets.

Live attenuated vaccines have also been contemplated in the art. Non encapsulated isogenic mutants of Streptococcus suis serotype 2 have been clearly shown to be avirulent. Yet, a live vaccine formulation based on a non encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of Streptococcus suis serotype 2." in: Vet Microbiol. 2002, 84:155-168.)

In the last years, an extensive list of antigenic or immunogenic Streptococcus suis molecules has been reported, and most of these have been discovered through immuno proteomics using either convalescent sera from infected pigs or humans and/or laboratory-produced immune sera. WO2015/181356 (IDT Biologika GmbH) has shown that IgM protease antigens (either the whole protein or the highly conserved Mac-1 domain representing only about 35% of the full protein) can elicit a protective immune response in piglets in a vaccination scheme of administering two doses of the IgM protease antigen, optionally in combination with a prime vaccination containing a bacterin. The data only show successful vaccination in piglets having an age of 5-7 weeks and receiving a challenge infection at an age of 9 weeks, thus well after the risk period (i.e. the period of peak incidence of pathogenic Streptococcus suis infections) of 2-3 weeks after weaning, i.e. 4-7 weeks of age. There is no indication whether the IgM protease antigen is able to overcome the common problem of interference with antibodies present in the animal to be vaccinated. On the contrary, the choice of animals being vaccinated at an age of 5-7 weeks, is a clear indication that the interference with maternally derived antibodies, if present, was meant to be avoided. So without any proof of effectiveness under practical circumstances (Streptococcus suis antibodies present during vaccination, and challenge infection in the window 2-3 weeks after weaning or transportation stress) it is still questionable whether the shown IgM protease/bacterin vaccine strategy is effective in practice. The same way, many licensed bacterin vaccines that are allowed on the market have inherently shown that they were effective in animal studies (otherwise they would not have been authorized to be commercially used), but they often fail to provide protection under practical, real-life circumstances. It is noted that WO2017/005913 (Intervacc AB) also describes the use of an IgM protease antigen (in particular, an IgM protease polypeptide fused to a nucleotidase) but only the property of being able to elicit a seroresponse has been shown. A protective effect for an IgM protease antigen is not shown in this international patent application.

OBJECT OF THE INVENTION

It is an object of the invention to find a vaccination strategy that is effective in protection of young piglets against Streptococcus suis (S suis) in the complete period of 2-3 weeks after weaning (i.e. in the complete period when the piglets have an age of 4-7 weeks). It is a further object to provide protection under the (common) circumstance that the subject animals to be vaccinated are seropositive for anti-S suis antibodies.

SUMMARY OF THE INVENTION

In order to meet the object of the invention a vaccine has been devised comprising an IgM protease antigen of *Streptococcus suis*, for use in a method wherein the vaccine is administered to a female pig in order to protect a piglet against *Streptococcus suis* through the intake of colostrum of the vaccinated female pig. Colostrum typically is taken within 48 hours, in particular within 24 hours after birth of the piglet in order to make sure high amounts of the maternally derived antibodies reach the circulatory system of the piglet by uptake of these antibodies through the intestinal walls.

Surprisingly, it has been found that by using an IgM protease antigen (thus even when using a vaccine that comprises as porcine antigen only the IgM protease antigen of *Streptococcus suis*), to induce antibodies in a female animal, piglets arrive at adequate protection against *Streptococcus suis* through the intake of colostrum of the vaccinated animal. For the first time now, an antigen that was shown to have a protective effect in piglets, has been shown to be useful for vaccinating sows to arrive at a clear protective effect in piglets, typically at least in the window of 2-3 weeks after weaning.

The invention also pertains to the use of an IgM protease antigen of *Streptococcus suis* for the manufacture of a vaccine for protecting a piglet against *Streptococcus suis*, by administering the vaccine to a female pig and allowing the piglet to take up colostrum form the vaccinated female pig. As indicated here above, to arrive at optimum protection, the colostrum is typically taken up within 48 hours, in particular within 24 hours after birth of the piglet.

It is noted that in a vaccine the antigen is typically combined with a pharmaceutically acceptable carrier, i.e. a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the vaccine.

BRIEF DESCRIPTION OF THE DRAWINGS

FIG. 1 depicts the pre-partus data in sows and the post-partus data in piglets.

DEFINITIONS

A vaccine is a pharmaceutical composition that is safe to administer to a subject animal, and is able to induce protective immunity in that animal against a pathogenic micro-organism, i.e. to induce a successful protection against the micro-organism.

An IgM protease antigen of *Streptococcus suis* is an enzyme that specifically degrades porcine IgM (and not porcine IgG or porcine IgA; Seele at al, in *Journal of Bacteriology*, 2013, 195 930-940; and in *Vaccine* 33:2207-2212; 5 May 2015), a protein denoted as IdeSsuis, or an immunogenic part thereof (typically having a length of at least about 30-35% of the full length enzyme). The whole enzyme has a weight of about 100-125 kDa, corresponding to about 1000-1150 amino acids, the size depending on the serotype of *S. suis*. In WO 2015/181356 several sequences that represent an IgM protease antigen of *Streptococcus suis* are given, viz. SEQ ID NO:1, SEQ ID NO:2, SEQ ID NO:6, SEQ ID NO:7 and SEQ ID NO:5, the latter being an immunogenic part of the full length enzyme (denoted as the Mac-1 domain, i.e. amino acids 80-414 of SED ID NO:7). Other examples of immunogenic parts of the full length enzyme are given in WO2017/005913. In particular the IgM protease may be the protease according to SEQ ID NO:1 of WO2015/1818356 or a protein having at least 90%, or even 91, 92, 93, 94, 95, 96, 97, 98, 99% up to 100% sequence identity in the overlapping regions. The amino acid sequence identity may be established with the BLAST program using the blastp alogorithm with default parameters. It is expected that the IgM protease of *Streptococcus suis* of various serotypes have a sequence identity higher than 90%, in particular expected to be 91, 92, 93, 94, 95, 96, 97, 98, 99% up to 100%. An artificial protein, for example made to optimize yield in a recombinant production system of the antigen, may lead to a lower amino acid sequence identity such as 85%, 80%, 75%, 70% or even 60% compared with the whole enzyme, while maintaining the required immunogenic function, and is understood to be an IgM protease antigen of *Streptococcus suis* in the sense of the present invention.

Protection against a micro-organism is aiding in preventing, ameliorating or curing a pathogenic infection with that micro-organism or a disorder arising from that infection, for example to prevent or reduce one or more clinical signs resulting from the infection with the pathogen.

EMBODIMENTS OF THE INVENTION

In a first embodiment of the present invention the piglet is protected during four weeks after intake of the colostrum. Preferably the piglet is protected during six weeks after intake of the colostrum, more preferably the piglet is protected during eight weeks after intake of the colostrum, and most preferably the piglet is protected during ten weeks after intake of the colostrum. Surprisingly, the present invention enables each of these embodiments although it is commonly known that even in the case maternally derived antibodies (MDA's) have shown to provide (some) protection, the level of these MDA's is generally considered to arrive at a non-protective level 4-5 weeks after intake of the colostrum, i.e. when the piglets have an age of 4-5 weeks. This means that S suis MDA's, even if protective, are commonly considered to be unable to protect a piglet during the complete period when the piglet is between 4 and 7 weeks of age, let alone between 4 and 10 weeks of age.

In another embodiment the method is for conferring protection against clinical signs associated with a pathogenic infection with Streptococcus suis. Typical clinical signs associated with a pathogenic infection with Streptococcus suis are increased rectal temperature, impaired locomotion (limping, swollen joints), increased respiration rate and neurological signs (e.g. tremors, convulsions, torticollosis, ataxia). Preventing, amelioration are curing one or more of these signs will be beneficial for the pig, not only since it is an indication that the pathogenic infection is being supressed.

In yet another embodiment the vaccine is for conferring protection against an increased mortality associated with a pathogenic infection with Streptococcus suis.

In still another embodiment the IgM protease antigen is present in an amount below 250 μg per dosis of the vaccine, preferably at 120 μg per dosis or below. The minimum amount is the amount at which protective immunity can still be obtained. This can be established by routine experimentation and depends i.e. on the immunogenic properties of the IgM protease antigen chosen but also on the required level of protection. For the current vaccine, a minimum amount is believed to be 1 μg of the antigen per dosis, but it may be any higher dosis such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or any higher integer in the range 61-119 up to and including 120 μg per dosis.

In an embodiment the female pig is vaccinated while being pregnant. Although it is foreseen that a female pig could receive adequate vaccination in between pregnancies in order to keep the level of antibodies (continuously) at an adequate height, it has shown to be useful to vaccinate the animal while being pregnant. In particular, it has shown to be useful to vaccinate the female pig in a period of 0-8 weeks before parturition, in particular in a period of 0-6 weeks before parturition, in both cases typically receiving the vaccine at least 1, 2 or 3 weeks before parturition.

In again another embodiment the female pig is vaccinated twice. It is recognized that it has been shown i.a. in European patent applications 17184626.4 and 17207758.8 (filed in the name of Intervet International BV) that a vaccination method consisting of administering only one shot of a vaccine comprising an IgM protease antigen of S suis is sufficient to confer protective immunity in the vaccinated animal and thus, that a booster vaccination may be omitted to arrive at the said protective immunity. It is therefore understood that also in the present method, one shot of the vaccine is sufficient to induce sufficient levels of anti-S suis antibodies in the female animal. However, vaccinating a female animal twice may even increase the levels of antibodies that ultimately arrive in the piglets through uptake of colostrum, and such strategy does not pose serious problems in the everyday practice of keeping adult animals. In such a two-shot regime, the first (prime) vaccination is typically boosted within 8 weeks from the first administration, commonly within 6, 4 or even within 2 weeks from the first administration.

EXAMPLE

Objective

The objective of this study was to test the efficacy of an IgM protease subunit vaccine in pregnant sows against Streptococcus suis challenge of the offspring at different ages, viz. at 4, 6, 8 and 10 weeks of age.

Study Design

For this study, 12 pregnant gilts were used. Six gilts were vaccinated at 6 and 2 weeks before estimated parturition with a recombinant Immunoglobulin M degrading enzyme of S. suis (rIdeSsuis) IgM protease antigen (Seele et al: Vaccine 33:2207-2212; 5 May 2015, par. 2.2.) at 120 μg per dose (as established by a Bradford protein assay using BSA as a standard) in XSolve adjuvant (MSD Animal Health, Boxmeer, The Netherlands). Six gilts were left as unvaccinated controls. After delivery the piglets of the sows were divided into four challenge groups of 20 piglets each (10 piglets from vaccinated sows and 10 piglets from control sows), providing an even distribution of the different litters over the groups. The four groups were challenged at 4, 6, 8 and 10 weeks of age, respectively with a virulent culture of S suis serotype 2. During 9-11 days after challenge the piglets were daily observed for clinical signs of S. suis infection such as depression, locomotory problems and/or neurological signs using a regular scoring system going from 0 (no signs) to 3 for severe cases. The same scoring system (0 for parameter not visible, the highest number for severe cases) was used for each parameter. Animals reaching the humane endpoint were euthanized. At regular times before and after vaccination (sows) and just before challenge (piglets) serum blood was collected for antibody determination. At regular times before and after challenge heparin blood was collected from the piglets for re-isolation of challenge strain. Thirteen weeks after booster vaccination, 4 sows were necropsied and the injection site was examined for local reactions or vaccine remnants.

Results

Four vaccinated sows were subjected to a post-mortem examination of the injection site. Two animals had a small (2-3 cm diameter) local reaction at the booster injection site consisting of a discoloration with increased tissue consistency. No abscesses or vaccine remnants were observed. It could therefore be concluded that the vaccine was safe to administer.

On day of first vaccination (6 weeks before estimated delivery) the gilts had (low) IgG antibody titres against the antigen. After vaccination, the vaccinated gilts showed a clear seroconversion whereas the control animals remained at a low level (see FIG. 1: Pre-partus data in sows, post-partus data in piglets). Average IgG titres in colostrum were 8.8 $\log_2$ higher in vaccinated animals as compared to the controls. After suckling, the piglets of the vaccinated dams had approximately 7.7 $\log_2$ higher serum titres compared to control animals. The difference in average titre at 4, 6, 8 and 10 weeks of age were 6.7, 5.3, 4.8 and 3.6 $\log_2$, respectively. The post challenge data for the period before euthanisation (days 9-11) are indicated in Table 1.

TABLE 1

Results post-challenge

| Age | Group | Clinical score (av) | # euth. per total | Survival time (av-days) |
|---|---|---|---|---|
| 4 weeks | Vaccine | 17.1 | 3/10 | 9.5 |
|  | Control | 31.6 | 6/10 | 8.0 |
| 6 weeks | Vaccine | 5.8$^a$ | 2/10$^b$ | 8.8$^a$ |
|  | Control | 59.7 | 9/10 | 2.7 |
| 8 weeks | Vaccine | 2.3$^a$ | 0/10$^b$ | 11.0$^a$ |
|  | Control | 59.5 | 8/10 | 4.7 |
| 10 weeks | Vaccine | 0.7$^a$ | 0/10 | 10.0 |
|  | Control | 15.6 | 2/10 | 8.8 |

$^a$significantly different from control group (Mann Whitney U test, $p < 0.05$)
$^b$significantly different from control group (Fisher's exact test, $p < 0.05$)

Conclusion

From the results it can be concluded that sow vaccination with the IgM protease subunit vaccine is an adequate vaccination strategy to control *Streptococcus suis* infections in piglets. The vaccine induced markedly better protection against *Streptococcus suis* challenge up to 10 weeks of age when compared with the protection arrived at in piglets receiving colostrum from naturally infected mother animals. This shows that the piglets can be protected in the complete period of 2-3 weeks after weaning, i.e. within the period when the piglets have an age of 4-7 weeks, and even beyond that period.

The invention claimed is:

1. A method of protecting a piglet against *Streptococcus suis* comprising administering a vaccine comprising an IgM protease antigen of *Streptococcus suis* to a female pig to induce antibodies in the female pig and thereby, make the female pig seropositive for anti-*Streptococcus suis* antibodies, in order to protect the piglet against *Streptococcus suis* through the intake by the piglet of the colostrum of the seropositive female pig.

2. The method of claim 1, wherein the piglet is protected against *Streptococcus suis* during a four week period after the intake of the colostrum.

3. The method of claim 1, wherein the piglet is protected against *Streptococcus suis* during a six week period after the intake of the colostrum.

4. The method of claim 1, wherein the piglet is protected against *Streptococcus suis* during an eight week period after the intake of the colostrum.

5. The method of claim 1, wherein the piglet is protected against *Streptococcus suis* during a ten week period after the intake of the colostrum.

6. The method of claim 1, wherein the method confers protection to the piglet against clinical signs associated with a pathogenic infection with *Streptococcus suis*.

7. The method of claim 1, wherein the method confers protection to the piglet against an increased mortality associated with a pathogenic infection with *Streptococcus suis*.

8. The method of claim 1, wherein the IgM protease antigen is present in an amount below 250 µg per doses of the vaccine.

9. The method of claim 1, wherein the IgM protease antigen is present at 120 µg per doses or below.

10. The method of claim 1, wherein the vaccine is administered to the female pig when the female pig is pregnant.

11. The method of claim 10, wherein the vaccine is administered to the female pig in a period of 0-8 weeks before parturition.

12. The method of claim 10, wherein the vaccine is administered to the female pig in a period of 0-6 weeks before parturition.

13. The method of claim 1, wherein the vaccine is administered to the female pig twice.

* * * * *